US006406890B1

(12) United States Patent
Mueller

(10) Patent No.: US 6,406,890 B1
(45) Date of Patent: Jun. 18, 2002

(54) PROCESS FOR THE AMPLIFICATION OF NUCLEIC ACID

(76) Inventor: Manfred W. Mueller, Schomergasse 30/3/16, 3400 Klosterneuburg (AT)

( * ) Notice: Subject to any disclaimer, the term of this patent is extended or adjusted under 35 U.S.C. 154(b) by 0 days.

(21) Appl. No.: 09/101,997

(22) PCT Filed: Jan. 15, 1997

(86) PCT No.: PCT/EP97/00160

§ 371 (c)(1),
(2), (4) Date: Mar. 10, 1999

(87) PCT Pub. No.: WO97/26368

PCT Pub. Date: Jul. 24, 1997

(30) Foreign Application Priority Data

Jan. 16, 1996 (DE) .......................................... 196 01 385

(51) Int. Cl.[7] ........................... C12Q 1/68; C12P 19/34; C12N 1/20
(52) U.S. Cl. ........................ 435/91.1; 435/6; 435/91.2; 435/252.3; 435/91.51; 435/91.52
(58) Field of Search ........................ 435/6, 91.2, 252.3, 435/91.51, 91.52

(56) References Cited

PUBLICATIONS

Chirpich, T. P., "Factors affecting terminal deoxynucleotidyl transferase activity in cacodylate buffer" *Biochem. Biophys. Res. Comm.* 78(4):1219–1226 (1977).

Deng G. R. and Wu R., "Terminal transferase: Use in the tailing of DNA and for in vitro mutagenesis" *Meth. Enzymol.* 100:96–116 (1983).

Edwards, J. et al., "Oligodeoxyribonucleotide ligation to single–stranded cDNAs: A new tool for cloning 5' ends of mRNAs and for constructing CDNA libraries by in vitro amplification" *Nucl. Acids Res.* 19(19):5227–5232 (1991).

Eschenfeldt, W. H. et al., "Homopolymeric tailing" *Meth. Enzymol.* 152:337–342 (1987).

Frohman, M. A. et al., "Rapid production of full–length cDNAs from rare transcripts: Amplification using a single gene–specific oligonucleotide primer" *Proc. Natl. Acad. Sci. USA* 85:8998–9002. (1988).

Hetzer, M. and Mueller, M. W., "PCR mediated analysis of RNA sequences" *Nucl. Acids Res.* 21(23):5526–5527 (1993).

Hultman, T. et al., "Direct solid phase sequencing of genomic and plasmid DNA using magnetic beads as solid support" *Nucl. Acids Res.* 17(13):4937–4946 (1989).

Roychoudhury, R., "Terminal labeling and addition of homopolymer tracts to duplex DNA fragments by terminal deoxynucleotidyl transferase" *Nucl. Acids Res.* 3(4):863–877 (1976).

Sambrook, J. et al., "In vitro amplification of DNA by the polymerase chain reaction" in: Molecular Cloning, A Laboratory Manual, 2nd ed., Cold Spring Harbor Laboratory Press, pp. 14.2–14.35 (1989).

Thrash, C. et al., "Cloning, characterization, and sequence of the yeast DNA topoisomerase I gene" *Proc. Natl. Acad. Sci. USA* 82:4374–4378 (1985).

Troutt, A. B. et al., "Ligation–anchored PCR: A simple amplification technique with single–sided specificity" *Proc. Natl. Acad. Sci. USA* 89:9823–9825 (1992).

*Primary Examiner*—W. Gary Jones
*Assistant Examiner*—Joyce Tung
(74) *Attorney, Agent, or Firm*—Paula A. Borden; Bozicevic, Field & Francis, LLP

(57) ABSTRACT

The present invention concerns a process for the amplification of nucleic acids, wherein the tailing of the nucleic acid to be amplified is effected by extending the nucleic acid with ribonucleotides at its 3' end with the aid of terminal transferase. Further, a kit for the amplification of a nucleic acid, which includes at least one ribonucleotide and terminal transferase, is provided.

Figure 1A:
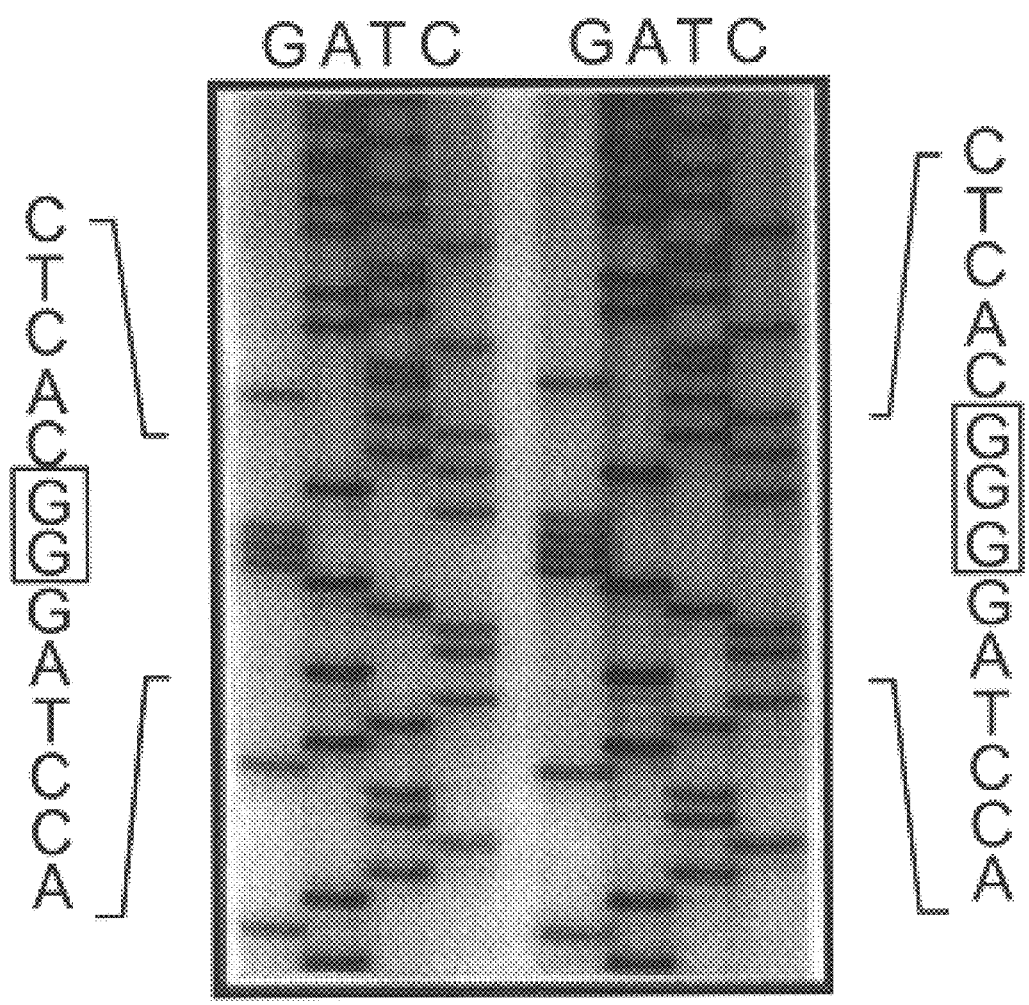

5 Claims, 5 Drawing Sheets mRNA specific primer

1. FIRST STRAND cDNA SYNTHESIS
(Reverse Transcriptase, RNase H-; Alkaline mRNA degradation)

2. RIBONUCLEOTIDE (rGTP) TAILING
(Terminal Transferase)

3. TAGGING OF RIBO-TAILED cDNA
(T4 DNA Ligase)

4. PCR AMPLIFICATION
(TAQ DNA Polymerase)

cDNA specific (nested) primer

5.1 DIRECT SOLID PHASE SEQUENCING
or
5.2 DIDEOXY-SEQUENCING OF CLONED PCR PRODUCT

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: reation substrate

<400> SEQUENCE: 1
gttaccattt taatacactt g     21

```
<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
aatacgactc actatag                                                    17

<210> SEQ ID NO 3
<211> LENGTH: 25
<212> TYPE: DNA
<213> ORGANISM: Artificial Sequence
<220> FEATURE:
<223> OTHER INFORMATION: reation substrate

<400> SEQUENCE: 3
gtgagacaag tataagtata ttatt                                           25

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtatatgtt atatataaac                                                 20

<210> SEQ ID NO 5
<211> LENGTH: 31
<212> TYPE: DNA
<213> ORGANISM: Artificial Sequence
<220> FEATURE:
<223> OTHER INFORMATION: mutagenic oligonucleotide

<400> SEQUENCE: 5
agcttgatat cgaattcgtg cagatactgc a                                    31

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gacgttgtaa aacgacggcc agt                                             23

<210> SEQ ID NO 7
<211> LENGTH: 44
<212> TYPE: DNA
<213> ORGANISM: Artificial Sequence
<220> FEATURE:
<223> OTHER INFORMATION: primer

<400> SEQUENCE: 7
aataagaatt cgcatgtcta attaggtata tgttatatat aaac                      44

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: (0)...(0)
```

```
<223> OTHER INFORMATION: n=t, a, g or c
<223> OTHER INFORMATION: reation substrate

<400> SEQUENCE: 8
ggtatatgtt atatataaan                                              20
```

PROCESS FOR THE AMPLIFICATION OF NUCLEIC ACID

This application is a 35 U.S.C. §371 filing of PCT Application No. PCT/EP97/00160, filed Jan. 15, 1997. This application claims priority benefit of German Patent Application No. DE 19601385.2, filed Jan. 16, 1996.

The present invention concerns a process for the amplification of nucleic acid and a kit for the amplification of nucleic acid.

A prerequisite for the analysis, particularly the sequence analysis, of nucleic acids is that the nucleic acid to be analysed is available in adequate quantities. Particularly with nucleic acids in very low concentrations, their sequence analysis presents a technical problem. The state of the technology knows many processes for amplifying scarce nucleic acids, i.e. those occurring in low concentration, before the analysis.

In particular, the analysis of the 5'-terminal coding region of RNA molecules causes difficulties. A very recent, widespread technique for the amplification of nucleic acids is based on the polymerase chain reaction (the so-called PCR technique) for the in vitro amplification of DNA (see Sambrook et al, Molecular Cloning, Laboratory Manual, $2^{nd}$ Edition, Chapter 14).

If the structure of RNA is to be elucidated, then before the actual amplification reaction a cDNA has to be prepared from the RNA to be analysed. In this, the problem often arises that the 5' end of the RNA is transcribed into cDNA with low frequency, and hence a sequence analysis is more difficult to obtain than [for] more 3'-located RNA sections.

The state of the technology describes several possibilities for amplifying the 5' end of RNA with the aid of the PCR technique. Common to most of these processes is that the first cDNA strand prepared from the RNA is extended at its 3' end by addition of further nucleotides, so-called "tailing", before the single-stranded cDNA strand is complemented to give the double-stranded cDNA.

As one possibility for the 3' tailing of DNA, the attachment of an oligonucleotide fragment to the free 3' end of cDNA or the polymerisation of desoxyribonucleotides onto the free 3' end has been described.

However, these known tailing processes have the disadvantage that the reaction is difficult to control, the yields of 3'-extended molecules sometimes do not satisfy the requirements, and undesirable by-products arise, in that for example several oligonucleotides become ligated to one another, and thus the 3' ends of different DNA molecules are not extended equally.

The technical problem on which the present invention was based was that of providing a further process for the amplification of a nucleic acid, with which the disadvantages arising from the state of the technology are not observed, and which in particular guarantees high efficiency in the 3' extension of nucleic acids.

The above problem is solved according to the invention by a process wherein the tailing of the nucleic acid is effected by reacting the nucleic acid to be amplified with a ribonucleotide in the presence of terminal transferase (also called terminal desoxynucleotidyl-transferase (TdT)).

This process, also referred to below as CRTC (controlled ribonucleotide tailing of cDNA), uses the extremely effective and well controllable RNA polymerising activity of terminal transferase under normal tailing conditions. The normal tailing conditions are for example described in Deng G R and Wu R (1983), Methods in Enzymology, 100: 96–116 and Roychoudkurg R et al. (1976), Nucleic Acids Res., 3: 863–877. This TdT activity adds a limited number of ribonucleotides, which are used as triphosphates (rNTPs) to the 3' end of a single-stranded or double-stranded nucleic acid, preferably a DNA. 2–4 ribonucleotides are preferably polymerised on.

In contrast to the primer-dependent DNA polymerase activity of TdT, which catalyses the repeated incorporation of desoxyribonucleotides (dNTPs) onto the 3' terminus of a single- or double-stranded DNA, desoxyribonucleotide tailing, the ribonucleotide tailing of a single-stranded DNA is influenced neither by the nature of the bases attached (rGTP, rATP, rUTP or rCTP) nor by the nature of the 3'-terminal nucleotide of the DNA primer ($G_{OH}$, $A_{OH}$, $T_{OH}$ or $C_{OH}$). Under standard conditions, an efficiency of more than 95% is achieved with the ribo-tailing of cDNAs according to the invention. rGTP is quite especially preferred for the ribo-tailing.

The creation of a short homopolymeric attachment made of ribonucleotides at the 3' end of the nucleic acid allows the unidirectional ligation of this nucleic acid, for example of a first cDNA strand, to a linearised plasmid DNA with a complementary 3' overhanging end in the presence of a ligase, preferably T4 DNA ligase. Hence the process according to the invention renders superfluous the attachment of a section of homopolymeric desoxyribonucleotides, which is often difficult to optimise and to control and commonly leads to nonspecific PCR products, and the process according to the invention also avoids the problems which arise in the ligation of a single-stranded oligonucleotide (also called an anchor) to the 3' end of cDNAs using T4 RNA ligase.

In the process according to the invention, a single-stranded DNA, and quite particularly a cDNA, is preferably used, this being preferably derived from a poly-(A)+-RNA.

In a preferred embodiment of the process according to the invention, after the tailing step a further nucleic acid molecule is bound to the 3'-end of the extended nucleic acid molecule.

The further nucleic acid molecule is preferably a double-stranded DNA and possesses a 3' overhanging end, which is complementary to the 3' end of the nucleic acid molecule extended by the ribonucleotides. This complementarity between the further nucleic acid molecule and the extended nucleic acid molecule favours the desired attachment of the further nucleic acid molecule through its hybridisation to the 3' end of the extended nucleic acid molecule. This procedure is also described as "tagging".

In an especially preferred embodiment, the further nucleic acid molecule is a DNA vector or an adapter molecule (also called a linker), which preferably at the same time contains a recognition sequence for at least one restriction enzyme.

Further, it is preferred that the further nucleic acid molecule is not only hybridised, but also ligated, to the 3' end of the extended nucleic acid molecule, preferably with T4 DNA ligase.

In a particularly advantageous embodiment, the further nucleic acid molecule is at the same time the primer for the synthesis of a second DNA strand, which complements the first DNA strand. The synthesis of the complementary strand can take place before the actual PCR amplification step, so that firstly a double-stranded nucleic acid is obtained, which is then amplified with the conventional PCR technique. However, the synthesis of the complementary strand (second strand synthesis) can take place at the same time as the PCR amplification.

The process according to the invention is suitable for all processes wherein DNA adapters are used and/or dNTP tailing takes place by means of TdT (such as for example in processes using the PCR-Select-cDNA-Subtraction Kit of Clontech, published in CLONTECHniques, October 1995), but it is especially suitable for the sequence analysis of RNA, in particular for the detection of the 5' sequence of a sparsely occurring RNA.

Here it is firstly necessary that a first cDNA strand be prepared from the RNA to be analysed. This can be effected by processes known in the state of the technology. The single-stranded cDNA strand obtained is then amplified by the measures explained in detail above. The amplified double-stranded DNA obtained can next be subjected to conventional processes for the sequencing of DNA.

Furthermore, the present invention allows the provision of a kit for the amplification of any nucleic acid, the kit containing at least one ribonucleotide, preferably selected from rGTP, rATP, rUTP and rCTP, and the terminal transferase.

FIG. 1 shows the result of a ribonucleotide tailing of single-stranded DNA according to the invention.

0.02 pmole of a 5'-terminally $^{32}$P-labelled DNA oligonucleotide (21-mer; 5'-GTTACCATTTT AATACACTTG; SEQ ID NO:1) were incubated with rNTPs (ATP, CTP, GTP or UTP) in the presence of TdT under reaction conditions such as those described in more detail in the following description. The products were fractionated on a 20% poly (A)crylamide/8 M urea gel, autoradiographed and quantified using a PhosphorImager (Model 400 B, Molecular Dynamics).

More specifically, FIG. 1a shows the analysis of the 5' terminal sequences of RNAs, including the controlled ribonucleotide tailing of cDNAs, tagging, PCR amplification and the dideoxy standard sequencing process on the PCR products obtained and cloned. The vector sequences are shown printed in bold. The cDNA sequences are shown in italics. The GG and GGG nucleotides, which were attached to the 3' terminus of the cDNA sequences by the TdT-catalysed ribonucleotide tailing, are specified. The purification of the biotinylated PCR products, which are made in the processes described in more detail below, was performed with magnetic spherules, as described by Hultmann S, Staahl E, Homes M and Uhlen L (1989), Nucleic Acids Res. 17: 4937–4939. After double cleavage with SacI and EcoRI, the PCR products were incorporated into the corresponding restriction cleavage sites of a pBluescript II KS+phagmid (Stratagene) and subjected to the dideoxy standard sequencing process with a T7 primer (5'-AATACGACTCACTATAG; SEQ ID NO:2) in the presence of sequenase (Amersham Life Science).

Figure 1B:
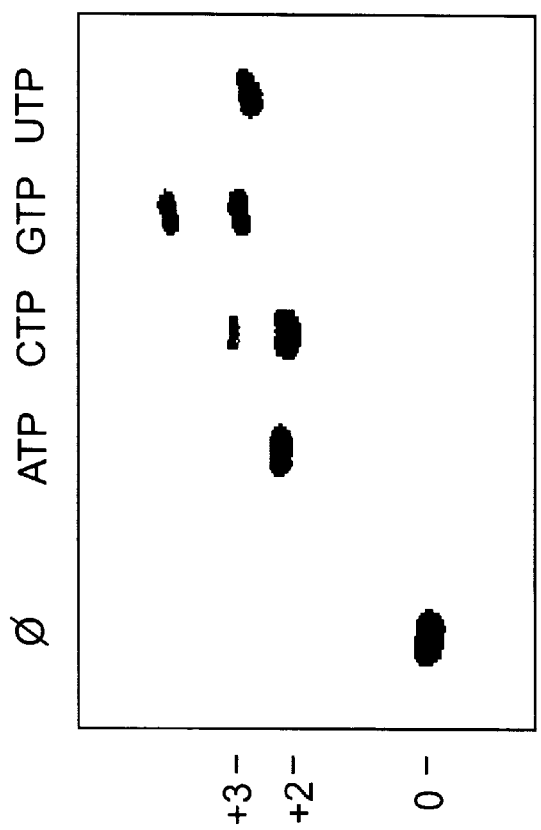

FIG. 1b shows the percentages of the unreacted fractions (0), of extended molecules (+2 to +4) and the total conversion (reacted fraction), depending on the rNTP used. φ signifies the control reaction in the absence of rNTPs. The nature of the reaction products, extended by two (+2) or three (+3) ribonucleotides, was confirmed by a PCR-mediated analysis of the RNA sequences, as described in Hetzer M and Mueller M W (1993), Nucleic Acids Res. 21: 5526–5527.

Figure 2:
Figure 2:
Figure 2:
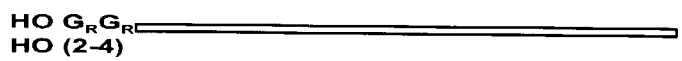
Figure 2:
Figure 2:
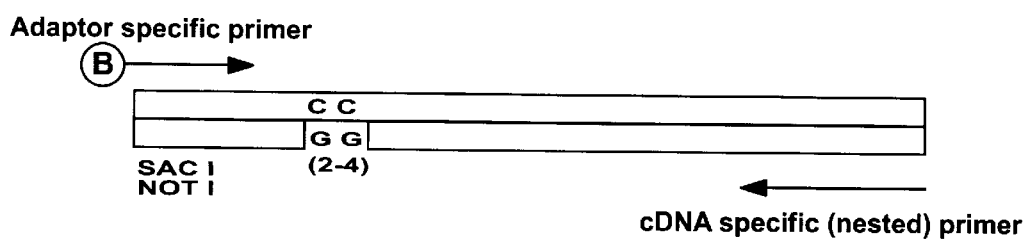

FIG. 2 shows the principle of the CRTC in the PCR-mediated cloning and sequencing of unknown 5' ends of a specific mRNA. The first step is the first strand cDNA synthesis from total-RNA or poly(A)$^+$mRNA, and it is performed with an mRNA-specific primer, which is 3' located (a known region in the 3' part of the mRNA matrix of an oligo(dT) primer). In the second step, the purified cDNA products are modified at their 3' ends by the attachment of two to four ribonucleotides (rGTPs) and in the third step they are applied to a specific double-stranded DNA adapter via a complementary 3' dinucleotide overhang (CC) in the presence of T4 DNA ligase. In the fourth step, the PCR amplification takes place with the use of an adapter-specific primer (this is 5'-terminally biotinylated) and a cDNA-specific "nested" primer, containing a desired restriction cleavage site; EcoRI in the case shown). The PCR amplification creates a unique PCR product, which is suitable for direct solid phase sequencing as described by Hultmann et al., (1989), Nucleic Acids Res., 17: 4937–4939, or for dideoxy sequencing after a cloning step using the restriction cleavage sites which derive from the DNA adapter (SacI, NotI as in the example) or from the cDNA primer.

Figure 3:
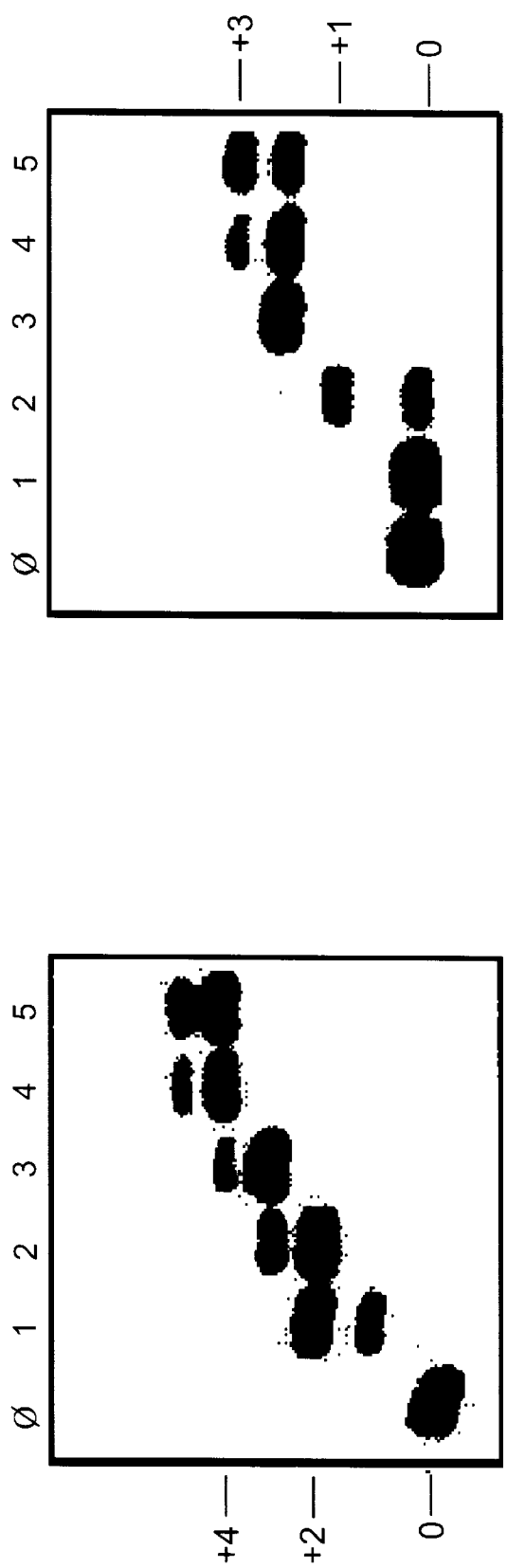

FIG. 3 shows the results of the rGTP tailing of cDNA under various conditions. Cacodylate buffer containing Co$^{2+}$ or Mg$^{2+}$ was used. 0.005 μM of a 5'-terminally $^{32}$P-labelled DNA oligonucleotide (25-mer, 5'-GTGAGACAAGTATAAG TATATTATT; SEQ ID NO:3) were incubated with a 10$^1$-fold to 10$^5$-fold excess of rGTP as the substrate in cacodylate buffer containing Co$^{2+}$ or Mg$^{2+}$ (1.5 mM) with excess enzyme at 37° C. for 60 minutes in a 10 μl reaction system. The products were fractionated on a 20% poly(A)crylamide gel/8M urea gel, autoradiographed and quantified (PhosphorImager Model 400B, Molecular Dynamics). The concentration of the rGTP substrates (1 to 5: 0.05 μM, 0.5 μM, 5 μM, 50 μM, 500 μM), the percentages of unreacted fractions (0) and the reacted fractions are shown for each of the metal ions used. Ø signifies the control reaction in the absence of rGTP.

Figure 4:
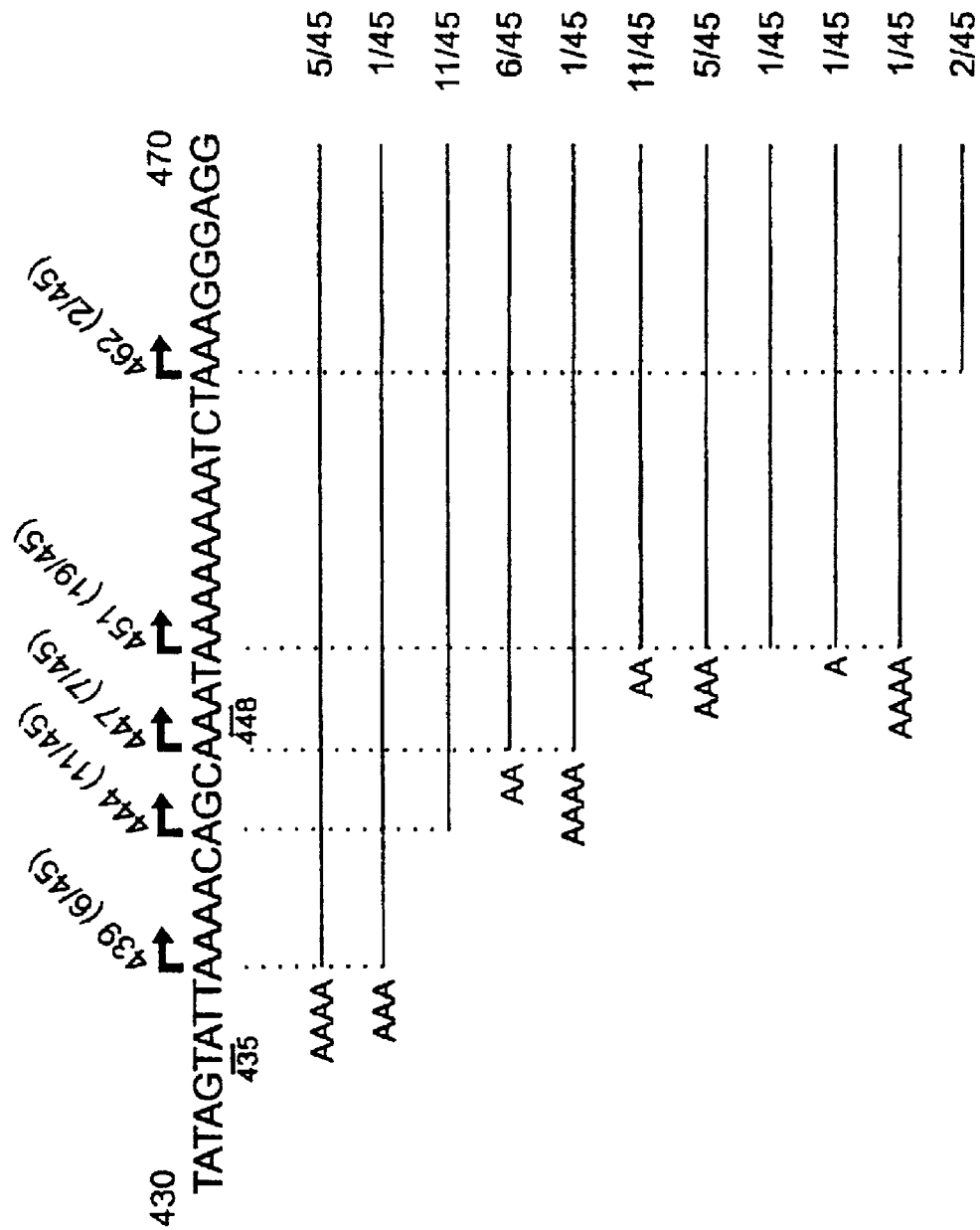

FIG. 4 shows the determination of the transcription start of the DNA topoisomerase I gene of yeast (Saccharomyces cerevisiae) by CRTC-mediated amplification of cDNA sequences. To locate the transcription start of the YSCTOPI gene (YSCTOPI; EC No. 5.99.1.2), starting from a poly(A)$^+$ mRNA population, the following variations in our standard protocol were used. (1) Poly(A)$^+$ mRNA (500 ng) from yeast strain DBY-746 (ClonTech) was subjected to a first strand cDNA synthesis with a primer which is specific for the minus strand of the DNA topoisomerase I (position 941 to 965). (2) The ribonucleotide tailing of the cDNAs was performed with rCTP (5 μM) in a 50 μl reaction. (3) An aliquot (10 to 20%) of the rC-extended cDNA products was ligated (tagged) with a complementary dG-dinucleotide-3'-overhang, wherein the overhang had been created by double cleavages (BsgIxXbaI) of the BSII/KS+IBsgI-plasmid (2.5 fmole). (4) The cDNAs (10%) provided with the vector were directly subjected to a PCR amplification (94° C., 20 seconds; 67° C., 60 seconds; 40 cycles) using the 5'-terminally biotinylated, vector-specific primer (M13 reverse; 25 pmole) and a YSCTOPI gene specific primer (position 706 to 727; 25 pmole) including an EcoRI site at its 5' end. After cleavage with EcoRI, the fragments obtained were cloned in the EcoRI site of a pBluescript II KS+ phagemid (Stratagene), and 45 clones were analysed by the dideoxy sequencing process using an automatic DNA sequencer (LI-COR 4000L).

Using this process, 5 individual transcription start sites on the YSCTOPI gene (EC-No. 5.99.1.2) were characterised (positions 439 (6/45); 444 (11/45); 447 (7/45); 451 (19/45) 462 (2/45). The deviations from the genomic sequence (the region of one to four T residues which are situated before the short piece of rCMP overhang at the 3' end of the DNAs) are represented as residues A. The two possible transcription start sites, which had previously been proposed by Thrash et al., Proc. Natl. Acad. Sci., USA, 82: 4374–4378 (1985), on the basis of theoretical considerations, are underlined.

The CRTC using terminal transferase described herein is an alternative strategy for amplification-based systems for cDNA cloning and mRNA sequence analysis. The recommended process offers several advantages compared to the normal dNTP tailing reactions and offers several improvements, when it is compared with other protocols for the PCR-based analysis of cDNA sequences. Firstly, in contrast to homopolymer tailing with dNTPs using terminal transferase (Eschenfeldt et al., (1987), Meth. Enzymol. 152: 337–342), CRTC is easy to control, self-limiting, since only two to four residues are attached, and extremely efficient. Under the reaction conditions recommended herein, a minimum incorporation of 85% is achieved; typical values lie in the range from more than 98%. Secondly, neither the extent of the reaction (conversion rate) nor the scale of the extension with rNTPs (number of rNTPs added) are strongly influenced by the ribonucleotides used as substrate; these parameters are also not strongly influenced by the nature of the terminal deoxynucleotide of the DNA primer. Finally, the use of a short homopolymeric ribonucleotide attachment at the 3' end of the cDNA allows the unidirectional ligation of a first-strand cDNA to a double-stranded DNA (linearised plasmid DNA or adapter) with a complementary 3' overhang in the presence of T4 DNA ligase. This process not only eliminates the need to use homopolymeric DNA attachments in amplification-based systems (RACE; rapid amplification of cDNA ends, see Frohmann et al., (1988), Proc. Natl. Acad. Sci., USA 85: 8998–9002), which is difficult to optimise and to control and often leads to a high background of nonspecific PCR products, but also avoids the problems which are caused by the ligation of a single-stranded anchor oligonucleotide to the 3' ends of cDNAs (SLIC: single-strand ligation of cDNA ends) with T4 DNA ligase (see Edwards et al., (1991), Nucleic Acids Res., 19: 5227–5232 and Troutt et al., (1992), Proc. Natl. Acad. Sci., USA 89: 9823–9825). In summary, it can be stated that compared to RACE or SLIC, the CRTC process according to the invention makes higher specificity and reliability possible in PCR-mediated analyses of mRNA sequences.

Under the recommended reaction conditions for the homopolymer tailing with rNTPs, the extent of the cDNA tailing is extremely efficient (>98%) and self-limiting, a controlled incorporation of two to four ribonucleotides at the 3' end of a cDNA taking place. The extent and the scale of the extension reaction can be varied as required by the selection of the concentration of the terminal transferase, the concentration of the cDNA ends in the reaction and the concentration of the rNTPs used as substrate. Under the conditions of a molar excess of enzyme over the DNA ends, the reaction is controlled by the enzyme, and the concentration of the cDNA termini has a slight influence on the extent of the reaction (see Eschenfeldt et al., see above). Thus with an excess of enzyme in the reaction mixture the concentration of the rNTPs only influences the degree of the extension reaction, but not the extent of the reaction. As a consequence, if desired, the degree of the rNTP incorporation can be reduced to one nucleotide by lowering the rNTP concentration in the reaction mixture.

Furthermore, the CRTC process according to the invention opens up the possibility of cloning the complete sequence of a poly(A)$^+$ mRNA. The specificity of oligo(dT) primers in the cDNA synthesis and the primer in the PCR often causes problems. The difficulties stem from the differing length of the homopolymeric poly(A) attachments. These problems can to some extent be solved by the use of an oligo(dT) primer with an additional specific sequence at the 5' end, as is done in the "RACE amplification" of cDNA ends (RACE: see Frohmann et al., (1988), Proc. Natl. Acad. Sci., USA 85: 8998–9002). The subsequent repeat amplification is then based on a primer which is directed towards a specific sequence. Alternatively, the oligo(dT) primer can be synthesised with two degenerate positions (3' (A, G, C, T) (A, G, C), this leading to a more precise hybridisation at the binding site between mRNA and poly(A)+ attachment in the first-strand cDNA synthesis. A combination of both the above alternatives increases the specificity, and therefore an oligo(dT) primer degenerate at the 3' terminus, containing additional specific sequences at its 5' end, is to be recommended in the first strand cDNA synthesis.

The following examples illustrate the invention:

For the analysis of an RNA, it is possible to start with a poly(A)$^+$-RNA with a 7-methyl-GTP (M7-GPPP).

First step: Synthesis of a First cDNA Strand and Purification Thereof

The synthesis of a first cDNA strand is based on known specific sequence information from the 3' region of the RNA to be analysed or the poly(A) attachment, which is present in most mRNAs. A sequence-specific primer or an oligo(dT) primer is used, in order to initiate the cDNA synthesis based on the mRNA matrix. After the degradation of the mRNA matrix by an alkali treatment, the purification of the cDNA is achieved using a silica matrix in a centrifugation vessel.

Second Step: Homoribonucleotide Tailing

The homoribonucleotide tailing of the first cDNA strand with TdT can be performed in the presence of any rNTP (rGTP, rATP, rUTP or rCTP). The purification of the 3' extended cDNAs and sample preparation is performed with a silica matrix in a column suitable for centrifugation.

Third Step: Tagging of the DNA

The single-stranded DNA, which is provided with two to four homoribonucleotides on its 3' end, is covalently ligated with a linearised vector DNA or a DNA adapter with a 3' overhanging end, which is complementary to the 3' end of the extended DNA. T4 DNA ligase is used for the ligation.

Fourth Step: PCR Amplification of the cDNA

The PCR amplification is performed with a 5'-terminally biotinylated first primer, which is specific for the vector or the adapter, and the cDNA primer as second primer, which was used in the synthesis of the first cDNA strand and which as a rule stems from the 3 ' region of the RNA. Optionally, another primer, stemming from the 3' region (nested primer) can also be used in its place. DNA polymerase, preferably Taq polymerase, is used as the polymerase.

Fifth Step: Sequencing of the Amplified DNA

For example, the direct solid phase sequencing of the amplified product can be performed using magnetic spherules as solid carrier (Hultmann S, Staahl E, Hornes M and Uhlen L (1989), Nucleic Acids Res. 17: 4937–4939) with a cDNA-specific primer in the presence of T7 DNA polymerase. Alternatively, the sequencing can be performed by the dideoxy process, either after the purification of the PCR product, or after a cloning step, in which the product is introduced into a vector in the desired orientation.

The following example describes in detail the sequence analysis of the 5' part of an RNA molecule (403 nucleotides long), which was prepared by in vitro transcription with T7 RNA polymerase.

(1) Synthesis of the first cDNA strand and purification of the sample. ssRNAs (0.1 pmole) extracted from gel, prepared by in vitro transcription of a PCR fragment containing a T7 promoter, were subjected to a cDNA synthesis with a sequence-specific primer from the 3' region of the RNA matrix (S3: 5'-GGTATATGT TATATATAAAC; SEQ ID NO:4) for 15 mins at 37° C., for which 10 units of SuperScript reverse transcriptase (RT: Gibco BRL) in a 20 μl reaction system, containing 50 mM tris HCl (pH 8.3), 75 mM KCl, 3 mM MgCl$_2$, 5 mM DTT and 0.3 mM dNTPs, were used. Directly after the synthesis of the first strand, the mRNA matrix was degraded under alkaline conditions (50 mM Na$_2$CO$_3$/NaHCO$_3$, pH 9.5; 30 mins, 95° C.). The purification of the cDNA product and the recovery of the sample in water (QD) was performed with a GlassMAX™ column (Gibco BRL), which is suitable for centrifugation.

(2) Ribonucleotide-tailing of cDNAs. 0.01 pmole of the purified cDNA product were incubated for 60 mins at 37° C. in the presence of 5 units of TdT (Boehringer Mannheim) and rGTP (Pharmacia). The incubation system had a volume of 10 μl and contained 200 mM potassium cacodylate, 25 mM tris HCl, 0.25 mg/ml BSA, pH 6.6 (TdT buffer, Boehringer Mannheim), 1.5 mM CoCl$_2$ and 0.5 μM rGTP. The purification of the cDNA extended at the 3' end was effected by an EtOH/NaAc (0.3 M) precipitation.

(3) Tagging of an rG-extended cDNA with a linear plasmid vector with a complementary 3' overhanging dC dinucleotide using T4 DNA ligase. 2.5 fmole of the rGTP-extended cDNA were incubated for 6 hrs or overnight at 16° C. with 2.5 fmole of a BsgI and EcoRI cleaved derivative (BSII/KS+/BsgI) of a pBluescript II KS+phagmid (Stratagene) in the presence of 1 unit T4 DNA ligase (Boehringer Mannheim) in a final volume of 20 μl of DNA ligase buffer as per the manufacturer's instructions (Boehringer Mannheim).

The BSII/KS+/BsgI derivative of the phagmid (Stratagene) was prepared via oligonucleotide mediated mutagenesis by replacement of the HindIII×PstI fragment in the cloning site of the phagmid by the 31-mer with the sequence 5'-AGCTTGATATC GAATTC GTGCAGATACTGCA; SEQ ID NO:5 (the BsgI site is underlined; the EcoRI site is italicised). The BSII/KS+/BsgI phagmid allows the blue-white selection; the cleavage with BsgI creates a single cleavage site with overhanging ends downwards (N16/N14) from the BsgI recognition site, a 3' overhanging dinucleotide (3'-CC) being created at the SmaI-BamHI site.

(4) PCR Amplification of the cDNA products from (3): 2 μl of the ligated mixture were directly subjected to the PCR amplification using the standard techniques (94° C., 20 secs; 58° C., 20 secs; 72° C., 40 secs; 35 cycles) in a 50 μl reaction system, 1 unit of Taq DNA-polymerase (Boehringer Mannheim) and buffer conditions as recommended by the manufacturer (Boehringer Mannheim) being used. 215 bp to 216 bp fragments were obtained as amplified PCR products. The PCR primers used were: a BSII/KS+/BsgI specific minus strand primer (M13-20 PCR; 5'-GACGTT GTAAAACGACGGCCAGT; SEQ ID NO:6; 26 pmole; 5-terminally biotinylated); a cDNA specific plus strain primer (S3-PCR: 5'-AATAAGAATTC GCATGTCTAATTAGGTATATGTTATATATAAAC; SEQ ID NO:7; 25 pmole) containing an EcoRI site (italicised) and partly complementary (underlined) to the 3' region of the cDNA sequence of the second strand.

(5.1) Direct solid-phase sequencing of the PCR products the purification of the PCR products and the sequencing by the dideoxy process using magnetic spherules as a solid carrier was performed as described in Hultmann S, Staahl E, Homes M and Uhlen L (1989), Nucleic Acids Res. 17: 4937–4939. The sequencing primers used were: S3: complementary to the 3' region of the second cDNA strand.

(5.2) Dideoxy sequencing of the cloned PCR products: the purification of the PCR products using magnetic spherules was performed as described in Hultmann et al. (see above). After double cleavage with SacI×EcoRI, the PCR products were introduced into the corresponding restriction cleavage sites of a pBluescript II KS+ phagmid (Stratagene) and subjected to the dideoxy standard sequencing process with a T7 primer in the presence of sequenase (Amersham Life Science) (see also FIG. 1).

The scale of the incorporation of two (13/20), three (7/20) or four (0/20) rGMP residues onto the 3' ends of the cDNAs correlated well with the values which were observed in the rGTP tailing reactions with single-stranded DNA primers in the presence of 0.5 μM substrate (+2, 68.7%; +3, 29.1%; see also FIG. 3).

Process for the Controlled Ribonucleotide (rGTP) Tailing of cDNA with Terminal Transferase 0.01 to 0.05 pmole of the purified (GlassMAX™ spin column, Gibco BRL) first-strand cDNA were incubated for 60 mins at 37° C. in the presence of 5.0 units TdT (Boehringer Mannheim) and rGTP (Pharmacia) in the following 10 μl reaction system: 200 mM potassium cacodylate, 25 mM tris HCl, 0.25 mg/ml BSA, pH 6.6 (TdT buffer, Boehringer Mannheim), 1.5 mM CoCl$_2$, 5 μM rGTP. These recommended conditions (cacodylate buffer containing CoCl$_2$, terminal transferase in molar excess over the concentration of the cDNA termini, $10^3$-fold excess of rGTP over cDNA 3' ends) are best suited for the incorporation of two to four rGMPs onto the 3' end of the single-stranded DNA (extent of conversion: 98.6%; extension by the reaction: +1 (0.0%), +2 (6.7%), +3 (71.9%), +4 (19.9%)). Decreasing the rGTP concentration in the reaction mixture to 0.5 μM promotes incorporation of two to three rGMPs (extent of conversion: 97.9%; extension by the reaction: +1 (0.0%), +2 (68.7%), +3 (29.1%), +4 (0.1%) see also FIG. 3). For most applications, rGTP concentrations in the range from 0.5 μM to 5.0 μM are recommended. The same protocol can essentially be used for all other rNTPs as substrate. The purification of the cDNA extended with ribonucleotides at the 3' end is effected by EtOH/NaAc (0.3 M) precipitation or alternatively by means of a Glass-MAX™ spin column (Gibco BRL).

Controlled Incorporation of Ribonucleotide Homopolymers at the 3' End of cDNA

In a first step in the controlled tailing of cDNA ends with ribonucleotides, a 5'-terminally $^{32}$P-labelled deoxynucleotide (21-mer) was used for the incorporation of a limited number of rNTP substrates. 0.02 pmole of this DNA primer in a cacodylate buffer [(CH$_3$)$_2$AsO$_2$], containing CoCl$_2$, with 5 μM rNTPs (rATP, rCTP, rGTP or rUTP), were incubated at 37° C. for 60 minutes under standard incubation conditions in the presence of TdT, as described for the dNTP tailing. As can be seen from FIG. 1b, under the conditions recommended for the dNTP tailing (Boehringer Mannheim), TdT catalyses an extremely efficient and controlled incorporation of the rNTP substrates onto the 3' end of a single-stranded DNA primer. In all test systems, an overall conversion rate of over 98% for the attachment of two to four rNMPs was obtained. The nature of the reaction products extended by two (+2) and three (+3) ribonucleotides was confirmed by PCR analysis of RNA sequences, as described by Hetzer M and Muller M W (1993), Nucleic Acids Res., 21: 5526–5527.

In the tailing reactions using dNTPs as substrate, the extent and the degree of the extension by the deoxynucleotides is a function of the concentration of enzyme, the concentration of the cDNA termini and the concentration of the selected dNTP, the buffer and the metal ion (see Chirpich T P (1977), BBRC 78: 1219–1226, Eschenfeldt W H et al.

(1987), Meth. Enzymol. 152: 337–342). Under the conditions of an enzyme excess, the concentration of the cDNA termini only influences the extent of the reaction slightly (Eschenfeldt et al, see above) and the reaction is decisively controlled by the enzyme. Under special potassium cacodylate buffer conditions for the ribotailing of the cDNA ends, further factors which determine the extent and the length of the reaction product are the rNTP concentration and the metal ion.

In addition, the influence of different concentrations of rGTP as the substrate in $Co^{2+}$- and $Mg^{2+}$-containing buffer systems on the extent and the length of the ribonucleotide tailing was studied. In $Co^{2+}$-containing reaction mixtures, when the rGTP concentrations were increased from the 10-fold excess over ssDNA ends to the 100-fold excess, the percentage of reaction products obtained and the length of the ribonucleotide attachment increased (FIG. 3). With a $10^2$- to $10^5$-fold excess of rGTP, only the length of the attachment was influenced, while the overall conversion of over 98% remained unchanged. In $Mg^{2+}$-containing buffer, a $10^3$- to $10^5$-fold excess of rGTP over the DNA ends was best suited for the incorporation of two to three rGMP residues.

Evidently under the special recommended conditions (e.g. cacodylate buffer containing $CoCl_2$, terminal transferase in molar excess over the concentration of the cDNA ends, $10^2$- to $10^3$-fold excess of rGTP over ssDNA), the ribonucleotide tailing is self-limiting, two to four rGMPs being incorporated (FIG. 3). In order to study this limited incorporation in more detail, single-stranded DNA primers, which had been extended by 2, 3 or 4 ribonucleotides, were extracted from the gel and subjected to a second round of dNTP tailing. A moderate and retarded repeated incorporation of deoxynucleotides was observed, when primers which had been extended by two ribonucleotides were studied (17% unreacted). DNA primers which had been extended by three (96% unreacted) or four ribonucleotides (99% unreacted) were practically inaccessible to further incorporation of dNTP substrates by terminal transferase. Conversely, if the ribonucleotide-extended DNA primers were studied in the presence of rNTP as the substrate, the reaction was self-limiting, and as the upper limit a total number of four incorporation reactions took place. These data show that under the recommended reaction conditions DNA primers with four rNMPs at the 3' end are inert to the incorporation of further nucleotides (dNTPs or rNTPs). Thus, the ribonucleotide extension of cDNA ends is easy to control owing to the self-limiting scale of the incorporation of the nucleotides.

In addition, it was studied whether the attachment of ribonucleotides is influenced by the 3' terminal nucleotide of the single-stranded DNA primer. For this purpose, four different variants of a 5'-$^{32}$P-labelled DNA oligonucleotide (20-mer; 5'-GGTATATGTTATATAT AAAN; N=T, A, G or C; SEQ ID NO:8) were analysed in the presence of rNTPs and TdT, as described above. A minimal incorporation of more than 85% was achieved if DNA primers which were provided with dG ends were used, the test being performed in presence of rUTP or rGTP as the substrate; typical values for the attachment of two to four rNMPs lay in the region of 98%.

All kinds of double-stranded DNA termini (3'-overhanging ends, smooth ends, 3'-shorter ends) can be extended with rNTPs as the substrate. As [for] the dNTP tailing reactions, the best reaction was achieved with 3'-overhanging ends.

Hence in summary it can be stated that these data show that—in contrast to the DNA polymerase activity of TdT— the ribonucleotide tailing of single-stranded DNAs proceeds very efficiently and is easily controllable because of the limited extent of the reaction. Further, the rNTP tailing is only slightly influenced by the nature of the added bases (rGTP, rATP, rUTP or rCTP) and at least not strongly influenced by the nature of the 3'-terminal nucleotide of the DNA primer.

Determination of the Transcription Start of the DNA Topoisomerase I Gene of Yeast (*Saccharomyces cerevisiae*) by CRTC, Starting from a Poly(A)$^+$ mRNA The CRTC described herein was used on mRNA of the DNA-topoisomerase I gene of *Saccharomyces cerevisiae* (YCSTOPI; EC No 5.99.1.2; see FIG. 4). Two possible transcription start sites, at positions 435 and 448, have been proposed by Thrash et al., (1985), Proc. Natl. Acad. Sci., USA, 82: 4374–4378).

Using the process according to the invention, five individual transcription start sites of the YSCTOPI gene were characterised (positions 439 (6/45), 444 (11/45), 447 (7/45), 451 (19/45) and 462 (2/45); see FIG. 4). As well as the incorporation of two to three rCMP residues on the 3' end of all the cDNAs analysed, several clones (31/45) contained sections of non-coding T-residues (one to four) on the C-terminus. Evidently the deviation from the genomic sequence is based on the action of reverse transcriptase on the 3 end of the cDNA products, whereby it copies the terminal mRNA sequences by a foldback mechanism using the cDNA terminus as a primer.

---

What is claimed is:

1. A method for amplifying a single-stranded cDNA molecule comprising the steps of:
   a) reacting said single-stranded cDNA molecule with a ribonucleotide triphosphate in the presence of terminal transferase, thereby forming a tailed single-stranded cDNA reaction product;
   b) linking the 3' end of said tailed single-stranded cDNA reaction product with a double-stranded adaptor nucleic acid molecule having a 3' overhanging end which is complementary to said 3' end of said tailed single-stranded cDNA reaction product, wherein said adaptor nucleic acid molecule primes the synthesis of a DNA strand complementary to the single-stranded cDNA reaction product, thereby forming a tagged reaction product; and
   c) amplifying said tagged reaction product.

2. A method according to claim 1, wherein said cDNA molecule is complementary to a poly $A^+$ RNA molecule.

3. A method according to claim 1, wherein said adaptor nucleic acid molecule is ligated to the 3' end of said tailed reaction product in a reaction catalyzed by a ligase.

4. A method according to claim 1, wherein said tagged reaction product is amplified by a polymerase chain reaction.

5. A method of determining a nucleotide sequence of an RNA molecule, comprising the steps of
   a) preparing a cDNA strand with said RNA as a template;
   b) amplifying said cDNA by the method according to claim 1; and
   c) sequencing the amplified cDNA.

* * * * *